(12) United States Patent
Keenan

(10) Patent No.: US 7,809,433 B2
(45) Date of Patent: Oct. 5, 2010

(54) METHOD AND SYSTEM FOR LIMITING INTERFERENCE IN ELECTROENCEPHALOGRAPHIC SIGNALS

(75) Inventor: Barry Keenan, Sherman Oaks, CA (US)

(73) Assignee: adidas AG (DE)

( * ) Notice: Subject to any disclaimer, the term of this patent is extended or adjusted under 35 U.S.C. 154(b) by 823 days.

(21) Appl. No.: 11/200,674

(22) Filed: Aug. 9, 2005

(65) Prior Publication Data

US 2007/0038382 A1 Feb. 15, 2007

(51) Int. Cl.
*A61B 5/0476* (2006.01)
*A61B 5/0488* (2006.01)
*A61B 5/0402* (2006.01)

(52) U.S. Cl. .................. 600/544; 600/509; 600/546

(58) Field of Classification Search ........... 381/94.1; 455/296; 600/323, 509, 510, 515, 544, 546; 607/45

See application file for complete search history.

(56) References Cited

U.S. PATENT DOCUMENTS

| | | | |
|---|---|---|---|
| 4,016,868 A | 4/1977 | Allison | 128/2.1 E |
| 4,306,567 A | 12/1981 | Krasner | 128/671 |
| 4,308,872 A | 1/1982 | Watson et al. | |
| 4,373,534 A | 2/1983 | Watson | |
| 4,433,693 A | 2/1984 | Hochstein | 128/721 |
| 4,452,252 A | 6/1984 | Sackner | |
| 4,456,015 A | 6/1984 | Sackner | |
| 4,463,764 A | 8/1984 | Anderson et al. | 128/719 |
| 4,648,407 A | 3/1987 | Sackner | |
| 4,753,988 A | 6/1988 | Henton et al. | 525/73 |
| 4,777,962 A | 10/1988 | Watson et al. | |
| 4,796,639 A | 1/1989 | Snow et al. | 128/719 |
| 4,800,495 A | 1/1989 | Smith | 364/413.03 |
| 4,807,640 A | 2/1989 | Watson et al. | |
| 4,815,473 A | 3/1989 | Watson et al. | |
| 4,817,625 A | 4/1989 | Miles | 128/721 |
| 4,834,109 A | 5/1989 | Watson | |
| 4,860,766 A | 8/1989 | Sackner | |
| 4,960,118 A | 10/1990 | Pennock | 128/200.4 |

(Continued)

FOREIGN PATENT DOCUMENTS

DE 4214263 11/1993

(Continued)

OTHER PUBLICATIONS

Hae-Jeong Park et al., "Automated Detection and Elimination of Periodic ECG Artifacts in EEG Using the Energy Interval Histogram Method", IEEE Transactions On Biomedical Engineering, vol. 49, No. 12, Dec. 2002, pp. 1526-1533.

(Continued)

*Primary Examiner*—Carl H Layno
*Assistant Examiner*—Luther G Behringer
(74) *Attorney, Agent, or Firm*—Sterne, Kessler, Goldstein & Fox, P.L.L.C.

(57) ABSTRACT

This invention provides methods and systems for removing or limiting interference and artifacts often found in EEG signals and/or EOG signals and/or other physiological signals, and produces output signals that can be of greater use for analytic or diagnostic purposes, such as sleep studies. Interference and artifacts are removed by applying a plurality of filtering methods targeted to the particular time-frequency characteristics of the anticipated interference.

28 Claims, 7 Drawing Sheets

U.S. PATENT DOCUMENTS

| | | | |
|---|---|---|---|
| 4,966,155 A | 10/1990 | Jackson | 128/671 |
| 4,972,842 A | 11/1990 | Korten et al. | 128/716 |
| 4,986,277 A | 1/1991 | Sackner | |
| 5,007,427 A | 4/1991 | Suzuki et al. | 128/659 |
| 5,040,540 A | 8/1991 | Sackner | |
| 5,074,129 A | 12/1991 | Matthew | 66/192 |
| 5,131,399 A | 7/1992 | Sciarra | 128/671 |
| 5,159,935 A | 11/1992 | Sackner et al. | |
| 5,178,151 A | 1/1993 | Sackner | |
| 5,301,678 A | 4/1994 | Watson et al. | |
| 5,331,968 A | 7/1994 | Williams et al. | |
| 5,348,008 A | 9/1994 | Bornn et al. | |
| 5,353,793 A | 10/1994 | Bornn et al. | |
| 5,416,961 A | 5/1995 | Vinay | 128/165 |
| 5,447,164 A | 9/1995 | Shaya et al. | 128/710 |
| RE35,122 E | 12/1995 | Coreman et al. | 600/633 |
| 5,533,511 A | 7/1996 | Kaspari et al. | 128/672 |
| 5,544,661 A | 8/1996 | Davis et al. | 128/700 |
| 5,564,429 A | 10/1996 | Bornn et al. | 128/696 |
| 5,577,510 A | 11/1996 | Chittum et al. | 128/709 |
| 5,588,425 A | 12/1996 | Sackner et al. | |
| 5,601,088 A | 2/1997 | Swanson et al. | 128/697 |
| 5,694,939 A | 12/1997 | Cowings | 128/671 |
| 5,719,950 A | 2/1998 | Osten et al. | 382/115 |
| 5,749,365 A | 5/1998 | Magill | 128/671 |
| 5,820,567 A | 10/1998 | Mackie | 600/519 |
| 5,848,027 A | 12/1998 | Dotter | 368/10 |
| 5,899,855 A | 5/1999 | Brown | 600/301 |
| 5,913,830 A | 6/1999 | Miles | 600/535 |
| 5,991,922 A | 11/1999 | Banks | 2/69 |
| 6,015,388 A | 1/2000 | Sackner et al. | |
| 6,047,203 A | 4/2000 | Sackner et al. | |
| 6,066,093 A | 5/2000 | Kelly et al. | 600/386 |
| 6,067,462 A | 5/2000 | Diab et al. | 600/310 |
| 6,068,568 A | 5/2000 | Kozakura et al. | 474/212 |
| 6,070,098 A | 5/2000 | Moore-Ede et al. | 600/544 |
| 6,142,953 A | 11/2000 | Burton et al. | 600/534 |
| 6,223,072 B1 | 4/2001 | Mika et al. | 600/510 |
| 6,254,552 B1 | 7/2001 | Lewis et al. | 600/603 |
| 6,261,238 B1 | 7/2001 | Graviely | 600/532 |
| 6,302,844 B1 | 10/2001 | Walker et al. | 600/300 |
| 6,341,504 B1 | 1/2002 | Istook | |
| 6,413,225 B1 | 7/2002 | Sackner et al. | |
| 6,436,057 B1 | 8/2002 | Goldsmith et al. | 600/586 |
| 6,449,504 B1 | 9/2002 | Conley et al. | 600/523 |
| 6,483,929 B1 | 11/2002 | Murakami et al. | 382/115 |
| 6,511,424 B1 | 1/2003 | Moore-Ede et al. | 600/300 |
| 6,551,252 B2 | 4/2003 | Sackner et al. | |
| 6,579,231 B1 | 6/2003 | Phipps | 600/300 |
| 6,604,115 B1 | 8/2003 | Gary, Jr. et al. | 707/104.1 |
| 6,633,772 B2 | 10/2003 | Ford et al. | 600/345 |
| 6,647,252 B2 * | 11/2003 | Smith et al. | 455/296 |
| 6,656,127 B1 | 12/2003 | Ben-Oren et al. | 600/532 |
| 6,721,594 B2 | 4/2004 | Conley et al. | 600/523 |
| 6,723,055 B2 | 4/2004 | Hoffman | 600/538 |
| 6,726,636 B2 | 4/2004 | Der Ghazarian | 600/532 |
| 6,727,197 B1 | 4/2004 | Wilson et al. | 442/301 |
| 6,747,561 B1 | 6/2004 | Reeves | 340/573 |
| 6,783,498 B2 | 8/2004 | Sackner et al. | |
| 6,801,916 B2 | 10/2004 | Roberge et al. | 707/101 |
| 6,881,192 B1 | 4/2005 | Park | 600/529 |
| 6,961,448 B2 | 11/2005 | Nichols et al. | 382/115 |
| 6,993,378 B2 | 1/2006 | Wiederhold et al. | 600/509 |
| 7,081,095 B2 | 7/2006 | Lynn et al. | 600/538 |
| 7,082,327 B2 | 7/2006 | Houben | 600/509 |
| 7,099,714 B2 * | 8/2006 | Houben | 600/509 |
| 7,104,962 B2 | 9/2006 | Lomask et al. | 600/529 |
| 2002/0084130 A1 | 7/2002 | Der Ghazarian | 600/532 |
| 2003/0135097 A1 | 7/2003 | Wiederhold et al. | 600/509 |
| 2003/0135127 A1 | 7/2003 | Sackner et al. | 600/536 |
| 2003/0185408 A1 * | 10/2003 | Causevic et al. | 381/94.1 |
| 2004/0030224 A1 | 2/2004 | Sotos et al. | |
| 2004/0111040 A1 | 6/2004 | Ni et al. | 600/534 |
| 2004/0143194 A1 | 7/2004 | Kihara et al. | 600/534 |
| 2004/0204636 A1 * | 10/2004 | Diab et al. | 600/323 |
| 2004/0210147 A1 * | 10/2004 | Houben | 600/509 |
| 2004/0249299 A1 | 12/2004 | Cobb | 600/529 |
| 2005/0054941 A1 | 3/2005 | Ting et al. | |
| 2005/0076908 A1 | 4/2005 | Lee et al. | 128/204.23 |
| 2005/0119586 A1 | 6/2005 | Coyle et al. | 600/538 |
| 2005/0228234 A1 | 10/2005 | Yang | |
| 2005/0240087 A1 | 10/2005 | Keenan et al. | 600/301 |
| 2005/0256385 A1 * | 11/2005 | Diab et al. | 600/323 |
| 2006/0036183 A1 | 2/2006 | Sackner et al. | 600/481 |
| 2006/0178591 A1 | 8/2006 | Hempfling | 600/529 |

FOREIGN PATENT DOCUMENTS

| | | |
|---|---|---|
| JP | 1091834 | 4/1989 |
| JP | 5168602 | 7/1993 |
| JP | 5298589 | 11/1993 |
| WO | WO2004/019503 | 10/2004 |
| WO | WO2005/115242 | 12/2005 |
| WO | WO 2007/021645 | 2/2007 |
| WO | WO 2007/089751 | 8/2007 |

OTHER PUBLICATIONS

Peter Anderer et al., "Artifact Processing in Computerized Analysis of Sleep EEG—A Review", Neuropsychobiology 1999; 40:150-157.

Fahrenberg et al., "Origins and Developments of Ambulatory Monitoring and Assessment", Progress in Ambulatory Assessment, Seattle, WA: Hogrefe and Huber (2001).

J. Sijbers et al., "Reduction of ECG and gradient related artifacts in simultaneously recorded human EEG/MRI data", Magnetic Resonance Imaging, vol. 18, pp. 881-886 (2000).

Dr. Rampil, Review Article: "A Primer for EEG Signal Processing in Anesthesia", Anesthesiology: vol. 89, Issue 4,—pp. 980-1002 (1998).

* cited by examiner

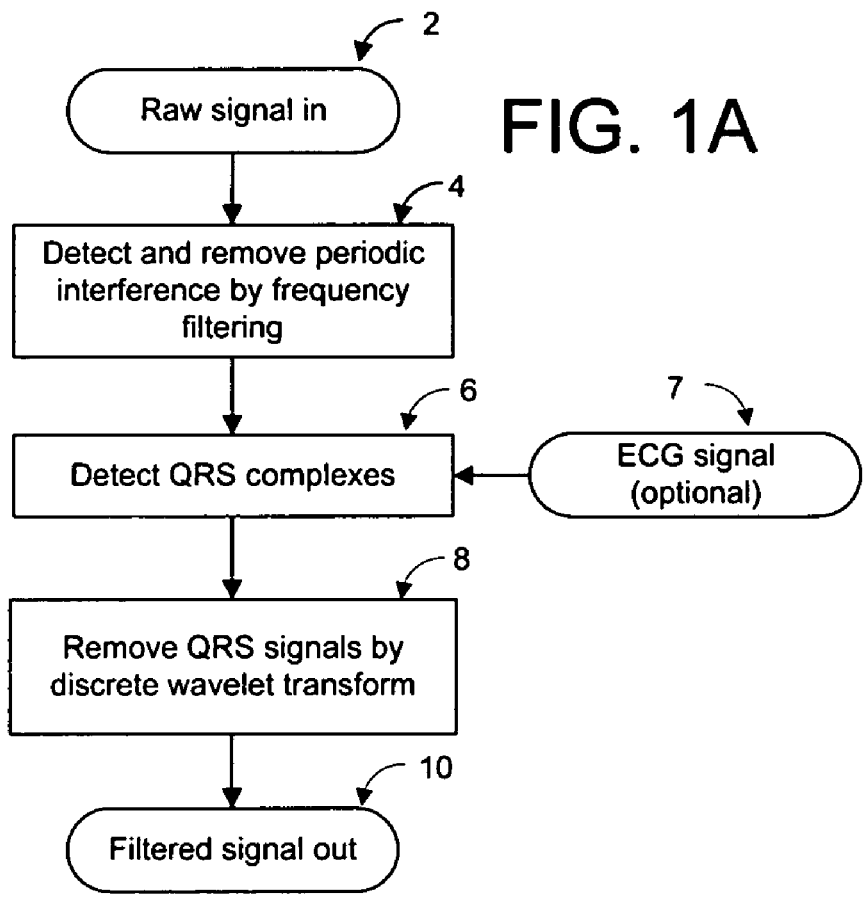
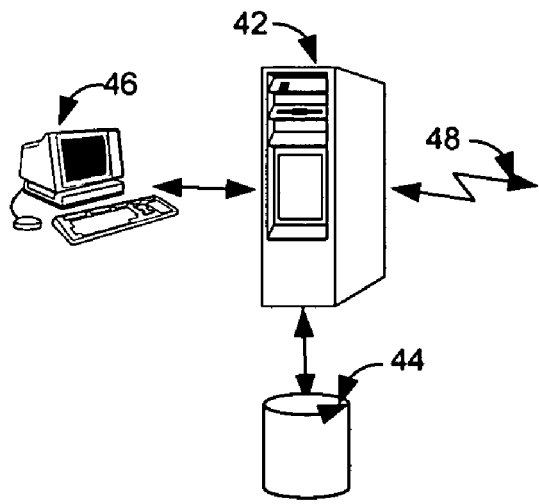

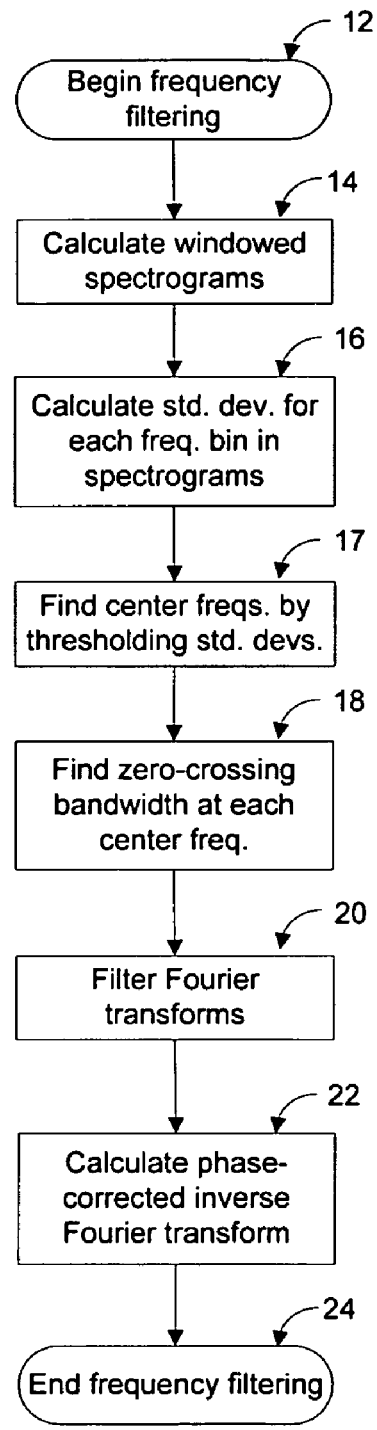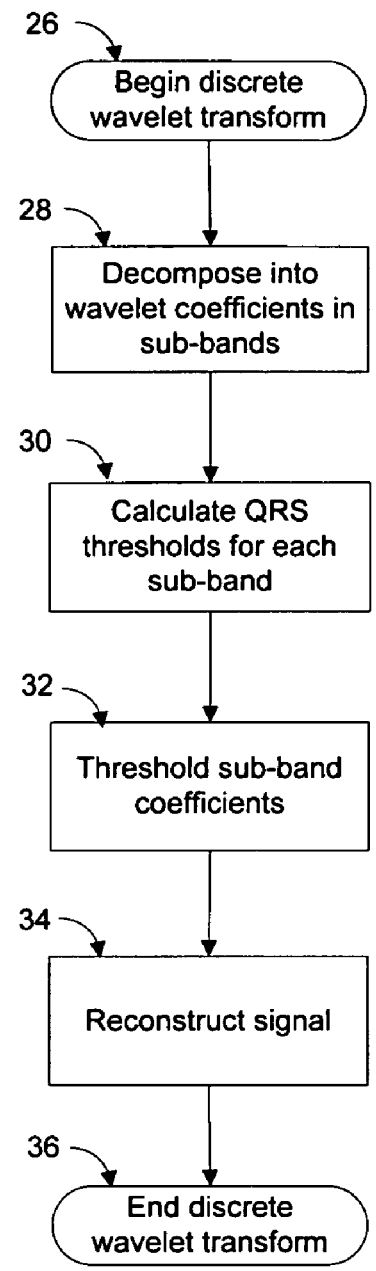
FIG. 2A
FIG. 2B

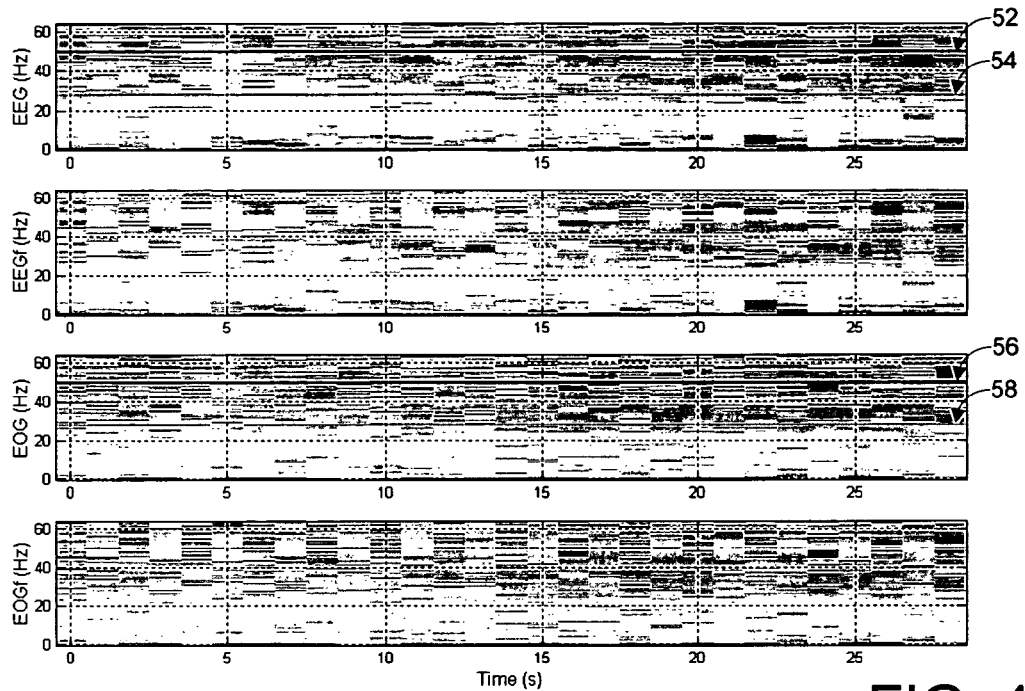
FIG. 4
FIG. 3A
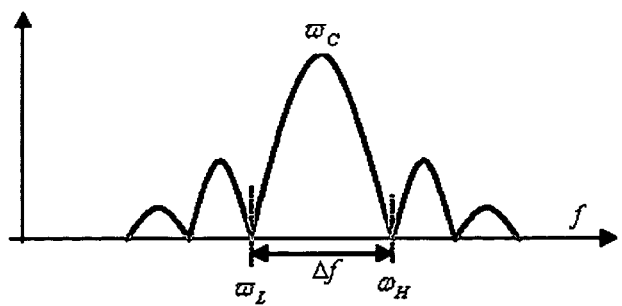
FIG. 3B
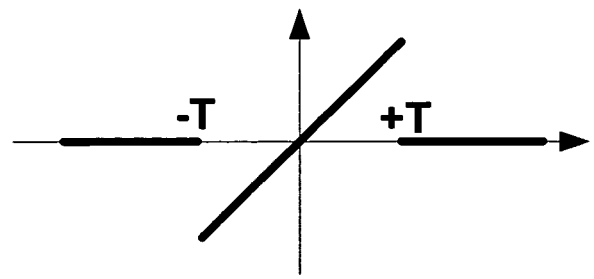

METHOD AND SYSTEM FOR LIMITING INTERFERENCE IN ELECTROENCEPHALOGRAPHIC SIGNALS

1. FIELD OF THE INVENTION

The present invention relates to the broad field of processing weak physiological signals, and more particularly to the field of processing electroencephalographic signals, especially electroencephalographic (EEG) measured during sleep studies. Systems and methods are provided for removing or limiting spurious signals and artifacts from weak physiological signals, such as EEG signals, electro-oculographic (EOG) signals and electromyographic (EMG) signals.

2. BACKGROUND OF THE INVENTION

Electroencephalographic signals (EEG) are exemplary weak physiological signals generated by electrical activity of the brain. EOG and EMG signals are similar and are generated by electrical activity, respectively, of the eye muscles or of muscles generally.

EEG recordings have a number of diagnostic and other uses. For example, as known in the art, sleep studies usually require determination of subject alertness, and because different alertness levels generate sufficiently characteristic EEG signals, subject alertness can be determined from EEG examination. EEG interpretation rules have been developed by which it can be determined that a subject is likely to be either awake, or drowsy, or sleeping, where sleeping itself can be classified as either stage I, stage II, stage III or REM. See, e.g., Rechtschaffen et al., eds., 1968, *A manual of standardized terminology, techniques, and scoring system for sleep stages of human subjects*. U.S. Dept. of Health, Education, and Welfare, Public Health Service.

EEG signals have a relatively broad band, routinely being measured over a bandwidth including at least the frequencies from 0.5-30 Hz or higher which is divided into sub-bands denoted, from the low to the high, as delta, theta, alpha and beta frequencies. See, e.g., Hill et al., 1963, *Electroencephalography*. London, McDonald. Additionally, mainly during sleep, EEG signals may include brief higher frequency bursts known as spindles, K complexes, and the like. Further, EEG signals have relatively low amplitudes, often no more than 10's of micro-volts. They are attenuated during conduction from their origin in the brain through tissue, bone and skin to their recording electrodes contacting the scalp.

These signal characteristics often lead to undesirable spurious signals and artifacts superimposed on the EEG signals of interest. See, e.g., Metting et al., 1990, High-quality recording of bioelectric events. I: interference reduction, theory and practice, *Med. & Biol. Eng. & Comput.*, vol. 28, pp. 389-397. First, conduction from the brain to the pick-up electrodes can reduce amplitudes and add noise, leading to lower signal to noise ratios. Second, because of their low amplitude and the often high impedance of their pick-up electrodes, spurious signals and artifacts arising from non-cerebral sources are easily picked up.

Spurious signals and artifacts found in the EEG can be usually seen to be either physiologic artifacts or non-physiologic artifacts. Physiologic artifacts arise from electrical activity elsewhere in the body, primarily in the heart or skeletal muscles. Cardiac artifacts are often found in EEG signals, most prominently in subjects with short and wide necks, and can be identified as higher frequency bursts synchronous with the QRS complexes of the electrocardiogram (ECG). Further, pulse artifacts can be induced in EEG electrodes placed over pulsating vessels. They can appear as slow waves generally similar to normal EEG activity, and can be identified since they usually trail QRS complexes by approximately 200-300 milliseconds. Skeletal muscle contractions also generate broad-band, low amplitudes electrical activity that can appear in the EEG such as from power supply lines (50 Hz generally, or 60 Hz in the US), fluorescent lights and a range of electronic devices in the vicinity of a subject. Metting et al., 1990.

Spurious signals and artifacts complicate EEG interpretation. EEG signals with significant artifacts may have to be entirely discarded. Lesser artifacts may make EEG signal interpretation more difficult or even lead to mis-interpretation. Accordingly, efforts have been directed to limiting or removing such artifacts.

These efforts include physical means, such as use of shielded electrode cables to limit pickup of non-physiologic artifacts. However, widespread clinical use of shielded cables has been hampered by their expense and by their often difficult and delicate setup. Since pickup of physiological artifacts can not be limited by such physical means, the prior art also includes efforts to remove artifacts by signal processing methods. See, e.g., Sahul et al., EKG artifact cancellation from sleep EEG using adaptive filtering, *J. Sleep Res.*, vol. 24A, pp 486; Park et al., 2002, Automated detection and elimination of periodic ECG artifacts in EEG using the energy interval histogram method, *IEEE Trans. Biomed. Eng.*, vol. 49, pp 1526-1533; and Anderer et al., 1999, Artifact processing in computerized analysis of sleep EEG—a review, *Neuropsychobiology* vol. 40, pp 150-7. However, these signal processing methods can unavoidably alter the EEG signals of interest, for example, by smoothing or limiting high frequency components.

Accordingly, there remains a need in the art for improved systems and methods for limiting or removing spurious signals and artifacts in EEG, and in weak physiological signals generally.

3. SUMMARY OF THE INVENTION

Objects of this invention include, therefore, providing novel and effective systems and methods for limiting or removing spurious signals and artifacts from weak physiological signals. The systems and method described herein expect that spurious components will have one or more predetermined generic characteristics, so that, if a component having an expected generic characteristic is present in an input signal, it can be recognized and specifically limited or removed from the output signal. Physiological information in a signal is preserved, because components not having one of the expected generic characteristics are not affected. For example, there is substantially no (or minimal) smoothing of the physiological signal.

The term "weak physiological signals" is understood herein to refer signals likely to have spurious, interfering components. For example, spurious, interfering components may arise because their amplitudes are comparable to intrinsic signal amplitudes, most often because the intrinsic signals are of low absolute amplitude. EEG signals are examples of signals with low absolute amplitude. Also, they may arise because the signal pickup means are sensitive to interference and ambient signals because they cannot be isolated sufficiently, or have high impedance, or the like. For example, ECG electrodes more optimized for patient tolerance and comfort may introduce spurious signals into even relatively high amplitude ECG signals that are absent when ECG measurements are made with electrodes more optimized for good electrical properties.

The invention preferably characterizes the signal components of interest in as well as any spurious components and/or interference by their "time/frequency domain" characteristics, in particular by their expected amplitudes in various regions of the "time/frequency domain". Accordingly, the term "time/frequency domain" as used and understood in this invention is now described. Generally, time/frequency domain analysis of a signal is understood herein to refer to decomposition of a signal into its various frequency components as they occur during various time periods. For example, a time/frequency domain may be simply represented in a two dimensional region, where time increases along one (horizontal) axis while frequency increases along a second orthogonal (vertical) axis. Then, the occurrence of particular frequencies during particular time periods are indicated by limited sub-domains within the overall domain. Intensities can be represented by, for example, shading, or coloring, or contouring, or the like of a sub-domain. Sub-domains of the time/frequency domain having various shapes ("characteristics") can be sampled by techniques known in the art. Sub-domains cannot be smaller than the limitation set by well known time-frequency uncertainty relations. Some sampling techniques sample more accurately in frequency and thus less accurately in sample time, that is they sample longer, thinner sub-domains; other techniques sample more accurately in time and thus less accurately in frequency, that is the sample more compact sub-domains or taller and narrower sub-domains.

The systems and methods of this invention are most advantageous where the input signals of interest have components broadly represented in the time/frequency domain, while the spurious components, artifacts, and/or interference to be removed or limited occupy only limited and pre-determined sub-domains of the time/frequency domain. Then, spurious components in an input signal are recognized when signal coefficients are found in the pre-determined sub-domains which have expected properties, and are removed or limited from the output signal by eliminating those signal coefficients that are likely to have arisen from spurious signal components. Since signal coefficients not likely to have arisen from spurious components are unchanged, signal components of interest will be altered no more that necessary to remove spurious components, and in many applications, will be substantially unaltered.

Time/frequency sub-domains of spurious signals can have various generic shapes. For example, spurious components arising from AC mains or nearby electronics often appear in one or more narrow frequency bands overlapping the bandwidth of the signals of interest. Such time/frequency sub-domains are generally long in a temporal dimension, for example, a significant fraction of signal duration, such as 50%, or 75%, or 100%, and generally short in a frequency dimension, for example, an insignificant fraction of signal bandwidth, such 15%, or 10%, or 5%, or less. Intermittently-occurring spurious signals that overlap signals of interest usually have differently shaped time/frequency sub-domains. These sub-domains are generally short in a temporal dimension, for example, an insignificant fraction of signal duration, such as 10%, or 5% or 1%, or 0.5% or less, and generally long in a frequency dimension, for example, a significant fraction of signal bandwidth, such than 20%, or 30%, or 40% or more. For sub-domains of all shapes, the time-frequency uncertainty relations require that the frequency dimension increase as the temporal dimension shrinks.

Signal components in a sub-domain can be identified as likely to arise from spurious signals if they are distinguishable in some manner from the physiological signals of interest. For example, spurious components can be substantially constant in time as compared to the time variations of amplitudes arising from physiological signals of interest. Also, spurious components can be identified because their amplitudes are substantially different (generally larger) from those of the physiological signals of interest. Comparisons of temporal variations, amplitudes variations, and the like can simply be done by establishing thresholds preferably depending on statistical measures such as means and standard deviations. Substantially constant spurious coefficients can be recognized when signal coefficients in such sub-domains have standard deviations in time less than typical standard deviations. For example, such spurious signal coefficients often have a "relative variation" compared to coefficients of interest of less than, for example, 1.5 or 1.0 or 0.5. Substantially larger spurious coefficients can be recognized when their relative values are larger, being for example, larger than 1.5, or 1.75, or 2.0 times the standard deviation from the means of the coefficients of interest.

A preferred (but not unique) measure of the shape of a sub-domain in the time/frequency domain is the ratio of the shapes relative temporal duration to the shapes relative frequency bandwidth. The relative temporal duration is the ratio of the temporal duration of the shape to the total temporal duration of the signal segment being processed. The relative frequency bandwidth is the ratio of the frequency bandwidth of the shape to the total frequency bandwidth of the signal segment being processed. This measure is less dependent on the absolute values of the durations and bandwidth of the signals being processed. For examples, narrow-band spurious signals have values of this ratio of 5 or greater, or 10 or greater, or 15 or greater, or 20 or greater, or more, while intermittently occurring spurious signals have values 2 of lesser, or 1 or lesser, or 0.1 or lesser, or 0.01 or lesser, or less.

Accordingly, interference is recognized when its generic characteristics are found in an input signal independently of frequency and independently of occurrence times. Thus, it is not necessary to know in advance the frequency of the interference or at what times it can appear in the signal. These types of spurious components can then be filtered by limiting of zeroing the signal amplitude in the sub-domains where the components are recognized.

Also, physiological signals often have unwanted QRS complexes (or other high amplitude electrocardiogram (ECG) wave) generated by cardiac activity. QRS complexes exemplify spurious components that, although having broader bandwidths, occur during non-overlapping time intervals and with known time courses, or "temporal signatures". (QRS complexes would, of course, not be filtered in applications where the ECG is a signal of interest.) The generic characteristics of this type of artifact include more square sub-domains, that is sub-domains with frequency bands and time durations that are of comparable sizes, and that match the time/frequency characteristics of the spurious components. They further include signal coefficients in these sub-domains that are consistent with the known signatures of the spurious components. For a simple example, if the amplitudes of spurious QRS complexes in an input signal consistently exceed the amplitudes of the signals of interest, they can be recognized where coefficients with larger than average amplitude occur in a suitable time/frequency sub-domain, that is in a frequency band that is typical of an isolated QRS complex for a time duration that is typical of an isolated QRS complex. If a concurrent ECG signal is available, searches for spurious QRS complexes can be limited to times in the vicinity of the QRS complexes—found in the ECG. This technique can be applied to other spurious components where their expected times of occurrence can be independently determined.

The second artifact type can be conveniently recognized, first, by performing wavelet decomposition of the input signal into a number of sub-bands that span the frequency bandwidth of the expected temporal signature. Next, the wavelet sub-bands spanning the temporal signature are searched in time increments typical of the duration of the temporal signature. Then, if wavelet coefficients are found that are consistent with the time course of the temporal signature (or that are simply unexpected in view of the surrounding coefficients) an artifact is likely to be present. Likely spurious components can then be limited or removed by zeroing of otherwise thresholding the wavelet coefficient arising from the likely artifact component. In the case of QRS complexes and similar signatures, only time increments in the vicinity of QRS complexes in a concurrent ECG need be searched.

The methods and systems of the invention do not change signal coefficients outside of the sub-domains found to contain interference or artifacts. Should the pre-selected characteristics be found in an input signal, only the corresponding coefficients of the input signal are limited or even set to zero; coefficients not arising from any spurious component is not changed. The processed coefficients are then "inverted" to restore associated signal values to their input values. Thereby, spurious signals and artifacts are removed without, e.g., smoothing the signal of interest. Unlike FIR or IIR filters, the non-corresponding portions are not linearly combined or otherwise altered. Instead only signal portions arising from the time and frequencies present in spurious components are changed.

Various embodiments of this invention can be constructed to filtering various signals, usually of physiological origin, in which one or more spurious signals, artifacts, or interferences have expected characteristics in the time/frequency domain. To construct an embodiment, appropriate sampling/filtering methods are first selected according to artifact time/frequency domain characteristics. To detect narrower band artifacts, Fourier transformation windowed with a Hamming window is more preferred. Other window function can also be used. To detect artifacts having more compact time/frequency sub-domains, wavelet decomposition is more preferred. Several wavelet families are known in the art, and an appropriate family is selected and scaled in time to best resolve the artifact to be filtered. Then an input signal is transformed/decomposed with the selected techniques into coefficients, and the resulting coefficients are searched to find occurrences of artifacts having one or more generic characteristics. Generic characteristics can include coefficients that are unusually constant, or unusually variable, or unusual large, or the like in comparison to global or local signal coefficients. Once an artifact occurrence is recognized, the coefficients likely to have arisen from the artifact are set to zero, thresholded, or otherwise limited. An output signal is reconstructed from the processed coefficients.

In its preferred embodiment, this invention has particular utility for processing electroencephalographic (EEG) signals or electrooculographic (EOG) signals electromyographic (EMG) signals or electrocardiographic (ECG) signals, and therefore can find use processing data from, for example, sleep studies, These signals often have periodic signal interference and/or ECG artifacts. In past sleep studies, a technician has often been to continuously monitor EEG and other signals, and if significant spurious components or artifacts occur, to correct recording methods by, for example, moving or reapplying recording electrodes. Because this invention can automatically minimize physiological and non-physiologic artifacts in these signals, need for continuous monitoring is reduced. Further, useful studies may be completed even when skin preparation or electrode placement alone are not ideal.

Specifically EEG signals have a broad time/frequency spectrum, occupying a 0.5-30 Hz frequency band more or less uniformly for the entire duration of the signal. Because they have low intrinsic amplitudes, they are prone to pick up spurious components from AC power sources, nearby electronics, and other sources of electrical signals. Such spurious components are usually narrow band, periodic and of substantially constant amplitudes, and can be limited or removed by the techniques discussed above Also, ECG activity is conducted through the body, and the QRS complex (or other high amplitude complexes) is often unavoidably sensed by the scalp electrodes used to sense the EEG (or EOG or EMG) signals. As discussed, the QRS complexes occur periodically during non-overlapping intervals signals by a concurrent ECG signal. All QRS occurrences have known substantially identical temporal signatures, and can also be limited or removed by the techniques already discussed.

For example, EEG signals (especially for sleep studies) are often analyzed in 30 sec. segments and in such segments often have total bandwidth of 50 Hz. EEG and other similar signals often contain spurious narrow-band interference from AC mains or nearby electronics. It has been found that such narrow-band signals often extend through substantially the entire duration of a segment but have a bandwidth of no more than 2-3 Hz. Thus, such signals generally have a temporal duration relative to the duration of a segment of approximately 100% but a bandwidth relative to the total segment bandwidth of approximately 4-6%. These narrow-band signals have a ratio of relative duration to relative bandwidth of approximately 20. EEG signals also often contain spurious intermittently-occurring QRS waves. In contrast to narrow-band interference, QRS waves have a typical temporal duration of approximately 0.1 sec, or a relative duration of approximately 0.3%, but they have a bandwidth approximately 10-30 Hz, or a relative bandwidth of approximately 40%. For QRS waves, the ratio of relative duration to relative bandwidth is approximately 0.01. For a nominal heart rate of about 60/sec., the total duration of all QRS waves together is approximately 10%, and even by this measure the ratio is less than approximately 0.3%.

Generally, one of skill in the art will understand how to select transform/sampling/filtering methods and to adjust their parameters so that broad spectrum physiological signals having characteristics similar to EEG and/or EOG and/or EMG signals and with spurious components having known characteristics in the time/frequency domain may be processed. This invention can filter spurious components with substantially no smoothing of the signal of interest, because it uses knowledge of the time/frequency domains characteristics of the spurious signals to specifically identify and remove them without altering the signals of interest.

Specifically, in one embodiment, this invention includes a method for processing a physiological signal of interest also comprising unwanted spurious signals, the method performing limiting at least one narrow-band spurious signal by performing one or more windowed Fourier transforms on one or more segments of said physiological signal, and filtering Fourier coefficients having temporal variation substantially less than the temporal variation of said physiological signal and having relative temporal duration substantially greater than relative frequency bandwidth, a relative temporal duration being a temporal duration in comparison to the temporal duration of the signal segment being processed, and a relative frequency bandwidth being a bandwidth in comparison to the bandwidth of the signal segment being processed; and also limiting at least one intermittently-occurring spurious signal by performing one or more wavelet transforms on one or more segments of said physiological signal, and filtering wavelet coefficients having characteristics that are distinguishable from said physiological signal of interest and having relative temporal duration substantially less than relative frequency bandwidth.

In another embodiment, the invention includes a method for processing a physiological signal of interest also comprising unwanted spurious signals, the method performing applying to one or more segments of said physiological signal one or more filters for filtering signal components present in sub-domains of the time/frequency domain plane having a plurality of different shapes, wherein at least one sub-domain has a shape with a relative temporal duration substantially greater than a relative frequency bandwidth, a relative temporal duration of a shape being a temporal duration of the shape in comparison to the temporal duration of the signal segment being processed, and a relative frequency bandwidth of a shape being a bandwidth of the shape in comparison to the bandwidth of the signal segment being processed, and wherein at least one sub-domain has a shape with a relative temporal duration substantially less than a relative frequency bandwidth;

These embodiments includes various aspects performing one or more of the following additional actions: determining whether signal components present in a time/frequency sub-domain arise from spurious signals, and limiting said signal components that arise from spurious signals; and limiting said signal components by setting an amplitude of said signal components to zero; and limiting said signal components by applying a threshold function to said signal components; and a signal component present in a time/frequency sub-domain is determined to arise from spurious signals if said signal component has a temporal variation in said sub-domain that is substantially less than the temporal variation of said physiological signal of interest; and wherein a signal component present in a time/frequency sub-domain is determined to arise from spurious signals if said signal component has characteristics that are statistically distinguishable from said physiological signal of interest; and wherein applying a filter for filtering signal components present in a time/frequency sub-domain having a shape with a relative temporal duration substantially greater than a relative frequency bandwidth further comprises performing a windowed Fourier transform; and wherein applying a filter for filtering signal components present in a time/frequency sub-domain having a shape with a relative temporal duration substantially less than a relative frequency bandwidth further comprises performing a wavelet transform.

These embodiments includes various further aspects performing one or more of the following additional actions: wherein said filtering Fourier coefficients further comprises determining the zero-crossing bandwidth of Fourier coefficients and limiting the amplitudes of Fourier coefficients within said zero-crossing bandwidth; and wherein wavelet coefficients are distinguishable if said coefficients have amplitudes greater than a threshold, said threshold varying in dependence on the amplitude of wavelet coefficients of said physiological signal of interest and on the amplitude of wavelet coefficients of said intermittently occurring spurious signal, said threshold varying in dependence on the means and standard deviations of said wavelet coefficient; and performing at least one inverse Fourier transform and at least one inverse wavelet transform, and outputting the signal resulting; and wherein said narrow-band spurious signals comprise signals having a relative temporal duration greater than or equal to approximately five times the relative frequency bandwidth of said signals, and said intermittently-occurring spurious signals comprise signals having a relative temporal duration less than or equal to approximately two times the relative frequency bandwidth of said signals and the total temporal duration of all occurrences of said intermittently-occurring spurious signals is less than or equal to approximately one-fifth of the total temporal duration of the signal segment being processed.

These embodiments includes various further aspects performing one or more of the following additional actions: wherein said intermittently-occurring spurious signals comprise at least one occurrence of a QRS wave; and wherein said threshold value is between a first expected amplitude of wavelet coefficients not in a vicinity of any QRS wave occurrence and a second expected amplitude of distinguishable wavelet coefficients in the vicinity of at least one QRS wave occurrence; and wherein vicinities of QRS wave occurrences are determined by a QRS detection method applied to a physiological signal; and wherein said first and/or second expected amplitudes are determined in dependence on the means and standard deviations of wavelet coefficients; and wherein said physiological signals comprise one or more of electroencephalographic (EEG) signals, and/or electrooculographic (EOG) signals, and/or electromyographic (EMG) signals.

Further embodiments are directed to computer systems for practicing the methods of this invention and to computer readable mediums comprising stored instructions for causing a processor to perform the methods of this invention, and to programs for performing the methods of this invention.

A number of references are cited here and elsewhere in this application. The entire disclosures of these references are incorporated herein in their entireties by reference for all purposes. Further, none of these references, regardless of how characterized herein, is admitted as prior to the invention of the subject matter claimed herein. In the following, and in the application as a whole, headings are used for clarity and convenience only and without any intended limitation.

4. BRIEF DESCRIPTION OF THE DRAWINGS

The present invention may be understood more fully by reference to the following detailed description of preferred embodiments of the present invention, illustrative examples of specific embodiments of the invention, the claims which recite various of the described embodiments and the appended figures in which:

FIG. 1A illustrates a preferred embodiment of this invention.

FIG. 1B illustrates an exemplary system for practicing this invention.

FIGS. 2A-B illustrate particular methods of the preferred embodiment.

FIGS. 3A-B illustrate aspects of the methods of the FIGS. 2A-B.

FIG. 4 illustrates an example of a signal spectrogram before and after filtering.

Figure 5:
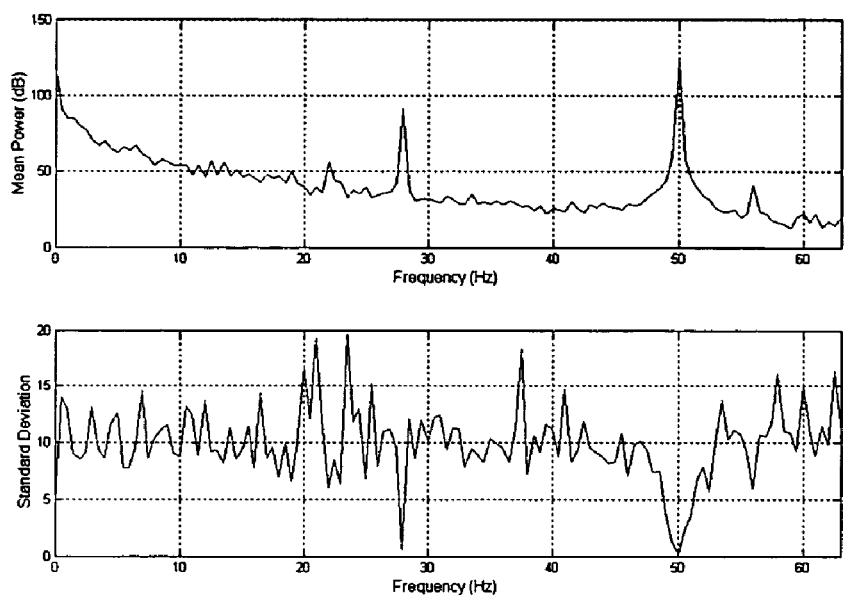

FIG. 5 illustrates an example of mean power and standard deviation per frequency bin for an EEG spectrogram.

Figure 6:
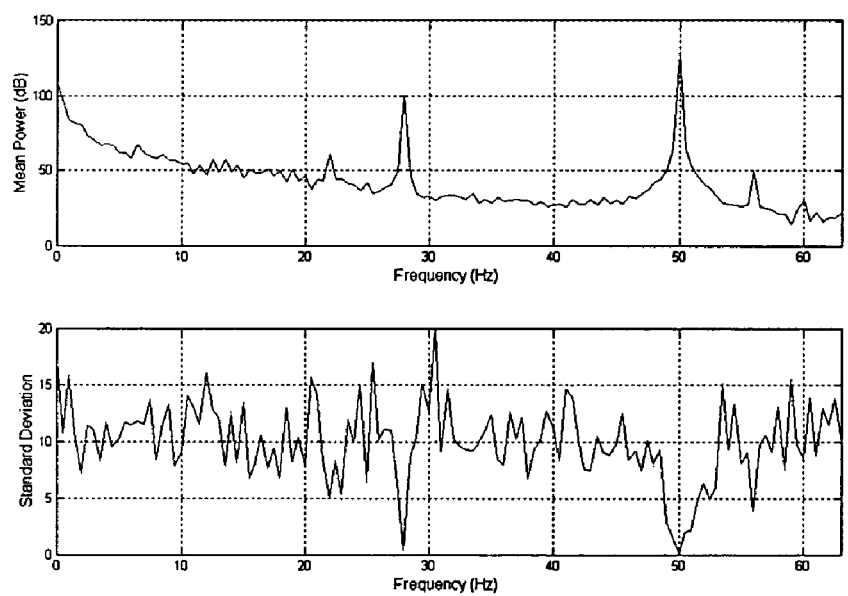

FIG. 6 illustrates an example of mean power and standard deviation per frequency bin for an EOG spectrogram.

Figure 7:
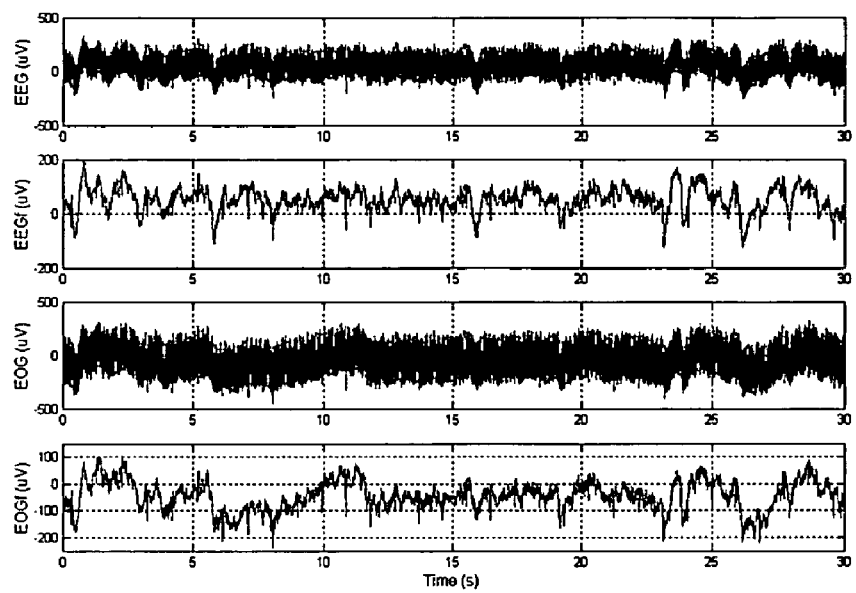

FIG. 7 illustrates an example of filtering periodic interference.

Figure 8:
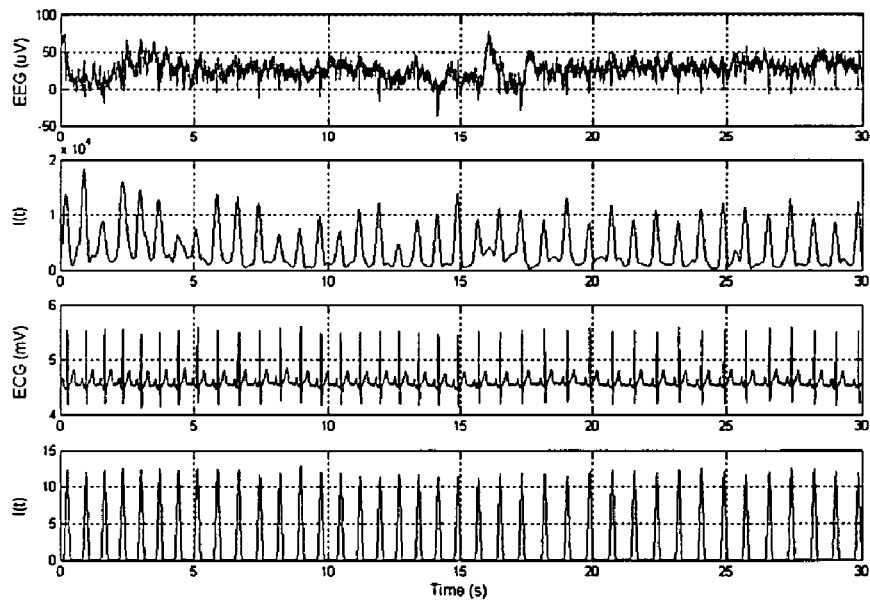

FIG. 8 illustrates an example of QRS detection in an EEG signal.

Figure 9:
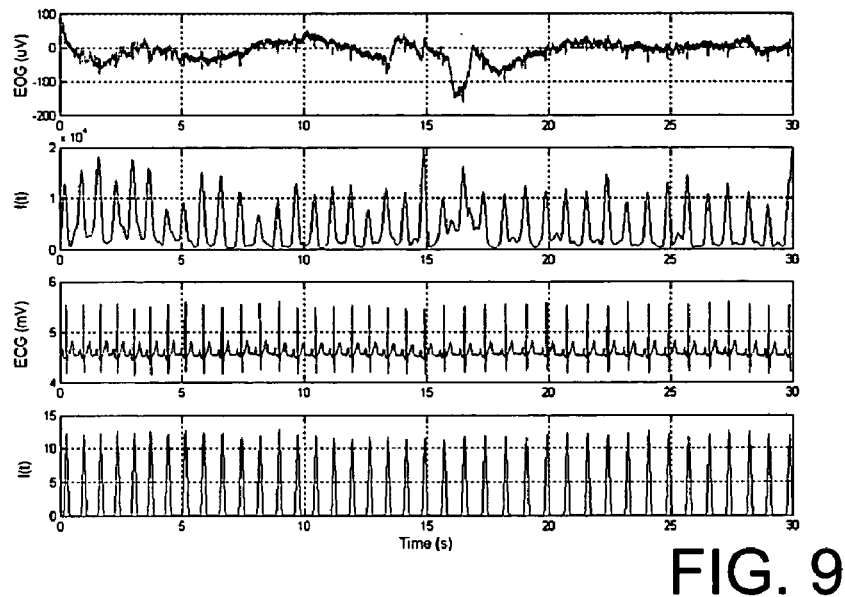

FIG. 9 illustrates and example of QRS detection in an EOG signal.

Figure 10:
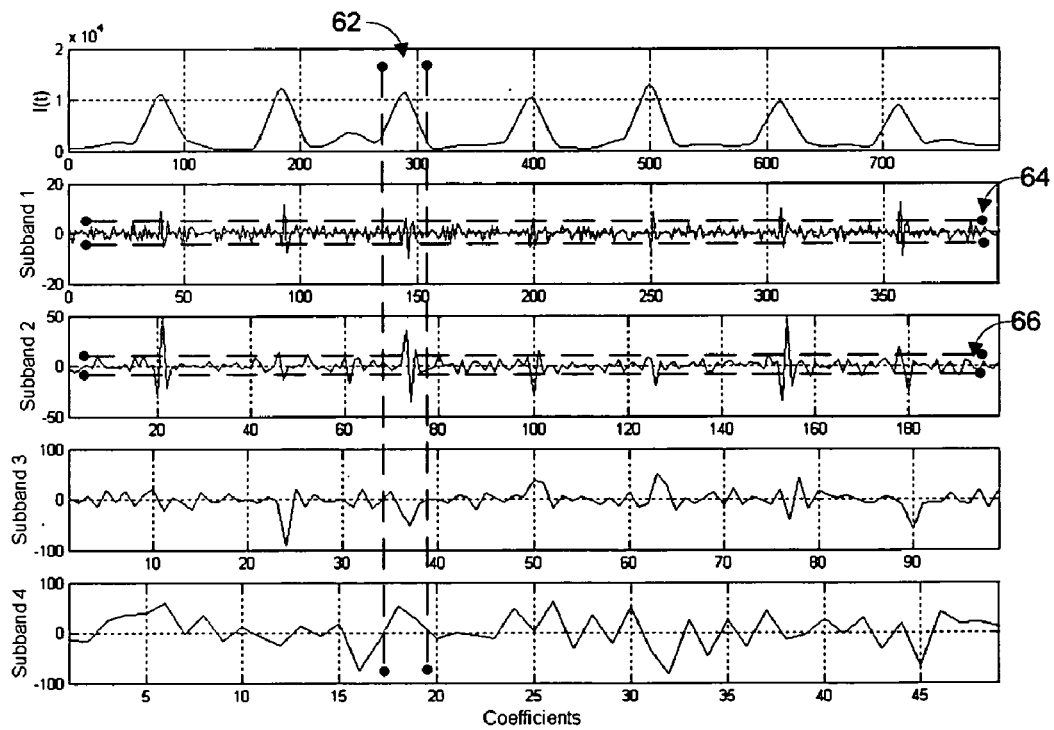

FIG. 10 illustrates and example of QRS and pulse detection by discrete wavelet transform.

Figure 11:
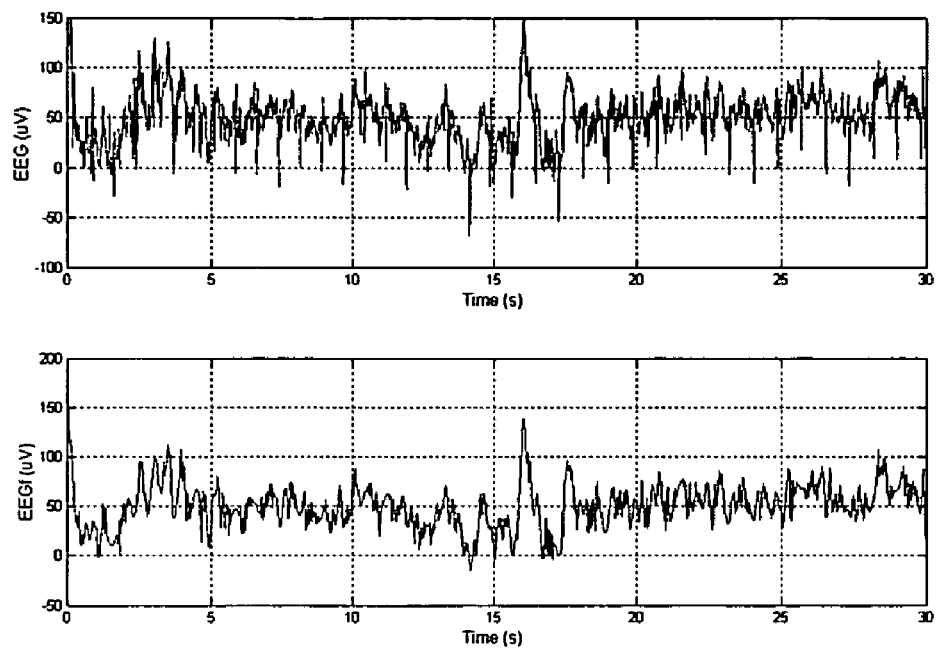

FIG. 11 illustrates and example of combined filtering periodic interference and filtering QRS complexes in an EEG signal.

Figure 12:
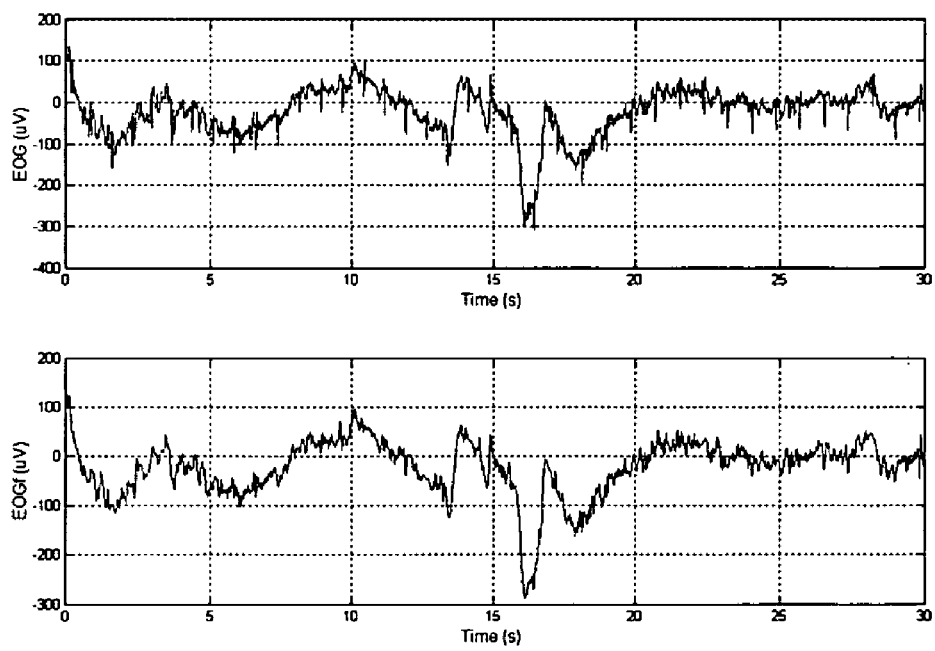

FIG. 12 illustrates and example of combined filtering periodic interference and filtering QRS complexes in an EOG signal.

5. DETAILED DESCRIPTION

A preferred embodiment of this invention processes EEG signals and/or EOG signals and/or EMG signals and/or other signals from sleep studies or generally. The detailed description is directed to the preferred embodiment solely for concreteness and brevity, and not with intended limitation. The embodiment described is only a preferred embodiment; one of skill in the art will understand how to apply the methods generally described above to process signals also generally described above to achieve results similar to those of the preferred embodiment.

A Preferred Embodiment

The preferred embodiment now described provides improved processing of, for example, EEG and/or EOG and/or EMG and/or other signals collected during sleep studies. It can process either pre-recorded signals, or real-time signals with a latency of approximately 15-30 sec. These signals are known to contain various types of spurious components, some of which are nearly periodic in the time domain and appear in narrow frequency bands in the frequency domain over a substantial fraction of the signal's total duration. Such signals usually arise from AC mains, fluorescent lighting, operation of nearby electronic equipment, and the like. The preferred embodiment operates in the frequency domain, preferably using windowed Fourier transforms, to detect and remove such spurious components from the output signal.

Other spurious components arise from physiological processes, for example, EEG (and also EOG and EMG) signals often have artifacts arising from the larger waves of the ECG, particularly the QRS complex that is conducted to the face and scalp and is picked up by EEG, EOG, and EMG electrodes. Spurious components of this type, including interference from other than cardiac sources, often are not limited to narrow frequency bands in the frequency domain, because although approximately periodic, their actual time signatures may be complex. The preferred embodiment operates in the time domain, preferably using wavelet decomposition, to detect such and limit such components from the output signal.

FIG. 1A summarizes processing of the preferred embodiment. First, periodic and narrow band interference is detected and removed 4 from the raw input physiological signal 2. Next, in order to guide removal of ECG signals, such as QRS complexes, the occurrence times of QRS complexes are detected 6. Often QRS occurrences can be detected by standard methods directly in the input EEG and/or other signals, as is preferred in sleep studies where a concurrent ECG signal may not be available. If a concurrent ECG signal 7 is available, QRS occurrences can be reliably detected therein. Finally, QRS and other ECG signals are detected in and removed from the output signal using the filtered signal from 4 and QRS occurrence times from 6. Thereby, the output signal has reduced periodic interference and limited ECG interference. Other processing sequences are within the invention's scope.

FIG. 1B illustrates an exemplary programmable system for practicing this invention. Here, the methods of this invention are encoded in a convenient computer language, for example, C, C++ and the like, or in a mathematical/statistical processing system, and are executed by processor 42. Data and encoded programs can be stored in computer readable memory 44. The encoded programs can be made available on removable computer readable media or by network connection. Collected EEG and/or other signals can be similarly made available, or can be input via link 48, either in real time with or offline from collection. Results can be presented to a user by means of display 46 or other user output devices.

This invention is useful is diverse applications whenever EEG and/or EOG (and other physiological) signals are collected, and different computer systems for practicing this invention can be tailored to the different needs of each application. In all applications, a processing device is needed, either a PC-type computer executing programs, or a firmware processor, for example, an ASIC or a FPGA. In the latter case, the methods of this invention will be encoded and loaded into the integrated device according to manufacturer's directions.

Removal of Periodic Interference

FIG. 2A illustrates in more detail the detection and removal of narrow band periodic interference (step 4, FIG. 1A). It is described herein in the preferred embodiment having parameters suitable for processing EEG and/or other signals. This invention is not limited to these particular parameters, and for other applications, other parameters can be selected.

Narrow band periodic interference in a generally broad-band signal, such as an EEG and/or other signal, can be detected by manual observation. This invention replaces such more cumbersome manual observation with a more automatic process, which detects narrow band periodic interference at a particular frequency if spectral energy at that frequency is found to be substantially consistently and constantly present throughout a substantial fraction of an observation period. To make such a finding, spectral energy samples are calculated by performing overlapping windowed spectrograms covering the observation interval. Spectral energy at a particular frequency (bin) is considered consistently and constantly present, and thus likely to be interference, if the normalized standard deviation (relative variation) of signal amplitude is less than a pre-determined threshold value. In contrast, spectral energy at a particular frequency bin arising from the broad band signal of interest generally has amplitudes that vary from sample to sample so that its standard deviation is greater than the pre-determined threshold.

Turning to the specific embodiment with parameters suitable for sleep studies, this process begins 12 with digitally-sampled EEG and/or other signals and calculates 14 a number of windowed spectrograms from these signals. Since EEG spectra often extend to and beyond 30 Hz, the sampling rate should be at least 100 Hz or preferably higher. First, the sampled signals are segmented into segments of 30 sec. duration. Such segments are widely used in sleep staging and are referred to as "epochs". Each segment is then windowed by multiplying the data values by overlapping window functions, and a spectrogram is calculated for each windowed segment. A Hamming window with 50% overlap is preferred, although other window functions with other overlaps (5%-75%) can be used. The fast Fourier transform is used with convenient vector lengths, for example, 256 elements. The windowed input signal is represented by $x(t_n,\tau)$, where $\tau$ identifies a window and $t_n$ identifies a time sample within a window, and the Fourier transform is similarly represented by $X(\overline{\omega}_n,\sigma)$ except that $\overline{\omega}_n$ represents a frequency bin. Performing a windowed spectrogram is then expressed by:

$$X(\overline{\omega}_n,\sigma) = F\{x(t_n,\sigma)\} \quad (1)$$

The spectrogram representing the spectral energy (in decibels) is then:

$$S(\overline{\omega}_n,\sigma) = 10 \log_{10}(|X(\overline{\omega}_n,\sigma)|^2) \quad (2)$$

Next, the process calculates 16 standard deviations of the spectral energy in each frequency bin over the windows in the observation period according to the formula:

$$\sigma(\overline{\omega}_n) = \sqrt{\frac{\sum_{i=0}^{i=k-1}(S(\overline{\omega}_n,i) - \overline{S(\overline{\omega}_n,i)})}{k-1}} \quad (3)$$

The sum here is computed over the window (second variable) number at a fixed frequency bin (first variable); $\overline{S(\overline{\omega}_n,i)}$ is the average of the spectral energy at the fixed frequency $\overline{\omega}_n$ over the windows, and k is an index identifying the windows. Alternately, a normalized standard deviation can be used, for example, the coefficient of variation which is the standard deviation divided by the mean.

Next, the process finds 17 the center frequencies of narrow band periodic as those frequency bins where $\sigma(\overline{\omega}_n)$ is less than or equal to a pre-determined threshold. For EEG and/or other signals collected during sleep studies, a threshold of 1 has been found suitable. In other applications, the threshold can be selected, for example, from test data so that observable narrow band periodic interference is found, while frequencies in the signal of interest are ignored, or by other means.

Next, the process finds 18 the zero crossing bandwidth at each center frequency found. Ideally, the zero crossing bandwidth about a center frequency $\overline{\omega}_C$ in a real spectra is the range of frequencies between the frequency $\overline{\omega}_L$ of the zero of the Fourier transform nearest $\overline{\omega}_C$ on the low frequency side and the frequency $\omega_H$ of the zero of the Fourier transform nearest $\overline{\omega}_C$ on the high frequency side. That is $\overline{\omega}_L \leq \overline{\omega}_C \leq \overline{\omega}_H$ and $F(\omega_L) = F(\omega_H) = 0$ and the zero crossing bandwidth is $\Delta\overline{\omega} = \overline{\omega}_H - \overline{\omega}_L$. FIG. 3A is an exemplary illustration of a simple real Fourier transform spectra with a zero crossing bandwidth identified.

Actually in observed spectra zero, the Fourier transform may not reach an exact zero and the zero crossing bandwidth about center frequencies may not be as clearly defined as in this exemplary illustration. Then, $\overline{\omega}_L$ and $\omega_H$ may be identifiable not as exact zeros of the spectra, but instead as the significant minima closest to $\overline{\omega}_C$ on the low and high frequency side, respectively. There values are determined by searching for such minima adjacent to $\overline{\omega}_C$ by known methods.

Narrow band periodic interference is then filtered 20 by zeroing the windowed Fourier transform in the determined zero crossing bandwidths about the found center frequencies. This is simply expressed by the following equation, where $|\hat{F}(\overline{\omega})|$ is the filtered Fourier transform absolute value:

$$|\hat{F}(\overline{\omega}_n)| = \begin{Bmatrix} 0, & \overline{\omega}_L \leq \overline{\omega}_n \leq \overline{\omega}_H \\ |F(\overline{\omega}_n)|, & \overline{\omega}_n \leq \overline{\omega}_L \,\&\, \overline{\omega}_H \leq \overline{\omega}_n \end{Bmatrix} \quad (4)$$

The phase of the Fourier transform, $\Phi[X(\overline{\omega})]$, is not altered by this filtering, for example, it is not zeroed in the zero crossing bandwidths. Thus the filtered Fourier transform is:

$$\hat{X}(\overline{\omega}_n) = |\hat{F}(\overline{\omega}_n)| e^{i\Phi[X(\overline{\omega}_n)]} \quad (5)$$

This phase corrected Fourier transform is then inverse Fourier transformed to recreate the signal of interest in the time domain.

QRS Detection

Knowing the occurrence times of heartbeats is useful in locating and removing interference of cardiac origin from EEG and/or other signals. Heartbeat occurrences are preferably recognized by detecting the QRS wave complex, either in an ECG signal if available, or otherwise in EEG and/or other signals themselves. Known QRS detection methods have been found suitable, such as the Pan-Tompkins detection algorithm. See, e.g., Pan et al., 1985, A real-time QRS detection algorithm, *IEEE Trans. Biomed. Eng.*, vol. 32, pp. 230-236. This algorithm bandpass filters an input signal, then differentiates the filtered signal, and lastly integrates the differentiated signal in order to create output pulses that are coincident with QRS complexes. FIGS. 5 and 6 illustrate the pulse output obtained from ECG, EEG and EOG signals.

Removal of QRS Signals

After narrow band periodic interference has been filtered, ECG and other cardiac pulse artifacts are limited or removed using wavelet thresholding techniques; alternatively, time-domain interpolation can be used.

Wavelets, signal decomposition and reconstruction using wavelets, and wavelet analysis techniques are described in numerous references of which the following are exemplary: Ogden, 1997, *Essential Wavelets for Statistical Applications and Data Analysis*, Birkhäuser, Boston, Cambridge Mass.; and Mallat, 1999, *A Wavelet Tour of Signal Processing*, Academic Press, San Diego Calif. Wavelet signal analysis has often been employed in the prior art to remove noise and similar interference, for example, by: decomposing an input signal into wavelet coefficients; distinguishing insignificantly small wavelet coefficients (usually appearing in the higher frequency sub-bands) arising primarily from noise and interference from significant wavelet coefficients arising from the signal of interest; filtering noise and interference by setting insignificant wavelet coefficients to zero, and then reconstructing an output signal from the significant wavelet coefficients.

However, in the present invention, the EEG and/or other signals of interest can appear somewhat noise-like, being usually of lower amplitude and broader spectrum and therefore appearing as wavelet coefficients that are smaller but generally more temporally uniform spread across several sub-bands often including higher frequency sub-bands. In contrast, the interfering QRS waves and/or other similar types of interference can appear as somewhat less noise-like. Such spurious signals can have significant amplitudes, often equal to or greater than the EEG and/or other signals of interest, and characteristic, periodic occurring temporal signatures. In the case of QRS interference, such interference generally appears in coincidence with QRS complexes detected in a concurrent ECG. Such spurious signals are often decomposed into larger wavelet coefficients occurring intermittently or periodically only in the wavelet sub-bands characteristic of their temporal signatures. Thus, the wavelet analysis used in the preferred embodiments of the present invention, in contrast to prior art wavelet analysis, zeros or limits larger, intermittently or periodically occurring wavelet coefficients that probably arise from spurious signals, while not altering smaller wavelets coefficients that probably arise from signals of interest.

QRS recognition and removal is illustrated in more detail in FIG. 2B. The signals input 26 to QRS removal are the EEG and/or other signals 24 from which narrow band periodic interference has been filtered (other processing orders may also be used in other embodiments). The input signals are first decomposed into wavelet coefficients for several wavelet sub-bands by iteratively processing them with a half-band high pass filter, h[n], and a half-band low pass filter, g[n]. Each iteration creates two wavelet sub-bands both sampled at half the original frequency. These filters are similar to half-band FIR filters; their precise characteristics are determined by the chosen wavelet basis. This processing is illustrated by the following equations, where $y_h[k]$ is the k'th high pass wavelet coefficient, and $y_g[k]$ is the k'th low pass wavelet coefficient:

$$y_h[k] = \sum_n x[n]h[2k - n] \qquad (6)$$

$$y_g[k] = \sum_n x[n]g[2k - n] \qquad (7)$$

It has been found suitable for EEG and/or EOG processing to use Daubechies (db4) wavelets which are applied first to the input signal and then iteratively re-applied to the successive lower sub-bands in order to create 4 levels of decomposition. Daubechies, 1988, *Comm. on Pure and Applied Math.*, vol. 41, 909-996. Generally, it is preferably to use a sufficient number sub-bands so that the frequency spectrum of the QRS temporal signature (generally, the temporal signature of the spurious signal to be limited) is completely covered. In the case of QRS interference, one or two sub-bands are generally not preferable because the QRS wave complex generally appears in three or more sub-bands.

QRS interference is limited or removed by "thresholding" 32 the wavelet coefficients in each sub-band. See, for example, Ogden, 1997; and Donoho, 1995, Denoising by soft thresholding." *IEEE Trans. IT*, vol. 41, pp. 613-627. It has been found sufficient to use the following thresholding function:

$$w_B[n] = \begin{cases} w_B[n], & |w_B[n]| \le T_B \\ 0, & |w_B[n]| > T_B \end{cases} \qquad (8)$$

where $w_B[n]$ is the n'th wavelet coefficient in the B'th wavelet sub-band and $T_B$ is the threshold for the B'th sub-band. FIG. 3B illustrates this function. It leaves coefficients less that the threshold, $T_B$, unchanged, because these are more likely to arise from the signals of interest. However, coefficients larger than the threshold are set to zero, because the latter are more likely to arise from QRS interference. Each sub-band may have a different threshold, $T_B$. Other thresholding functions that are known in the art can also be used in this invention. For example, wavelet coefficients less than $T_B$ may be non-linearly scaled. In another alternative, the thresholding function can be applied only in the vicinity of expected occurrences of the spurious signals. This alternative is advantageous where, as for QRS complexes, occurrences of the spurious signal are independently indicated.

Thresholds, $T_B$, are calculated 30 for each sub-band prior to coefficient thresholding 32. This calculation advantageously makes use of the determined QRS occurrences, since only wavelet coefficients in the vicinity of QRS occurrences can represent such interference. Many methods known in the art can be used to calculate $T_B$. For example, wavelet coefficient means and standard deviations for each sub-band can be computed in the time intervals between QRS occurrences, and $T_B$ for each sub-band can be set to be two (or one, or three) standard deviations above the relevant mean. Alternately, coefficient means and standard deviations for each sub-band can be computed only in the vicinity of QRS occurrences, and $T_B$ for each sub-band can be set to be two (or one, or three) standard deviations below the relevant mean. Yet another alternative calculates $T_B$ so as to lead to maximum reduction in wavelet coefficient power for each sub-band in the vicinity of QRS occurrences but with a minimum reduction in wavelet coefficient power between QRS occurrences for each sub-band. However determined, $T_B$ can be periodically updated, for example, every minute, 5 min., 30 min. or so forth.

Lastly, an output signal 36 is reconstructed 34 from the thresholded wavelet coefficients. Since the half-band filters used to determine the wavelet coefficients form orthonormal bases, reconstruction is simply the decomposition procedure followed in reverse. The wavelet coefficients at every sub-band are up sampled by two, passed through high pass g'[n] and low pass h'[n] synthesis filters which make up the inverse discrete wavelet transform (iDWT) appropriate to the type of wavelet used for signal decomposition. Reconstruction is illustrated by the following equation:

$$z[k] = \sum_n h'[n]y'[2k - n] + \sum_n g'[n]d[2k - n] \qquad (9)$$

where z[k] is the reconstructed signal and y'[n] and d[n] are the wavelet coefficient inputs to the reconstruction filter.

EXAMPLE

This section describes analysis according to the methods of this invention of single channel EEG and EOG data that was recoded from a sleeping subject under poor signal conditions. Also available was a single channel ECG signal.

Input signals were first processed to remove narrow band periodic interference according to the process illustrated in FIG. 2A. Input signals were first divided into 30 sec. segments (thirty second segments, known as epochs, being routinely used for sleep staging). Overlapping windowed spectrograms of the 30 sec. segments of EEG and EOG signals were calculated using a fast Fourier transform.

FIG. 4 illustrates the overlapping, windowed spectrograms in a time-frequency domain for both the input EEG and EOG signals (bands one and three in FIG. 4) and for the filtered EEGf and EOGf signals (bands two and four in FIG. 4). EEG band one demonstrates interference 52 of high and constant amplitude that was present throughout the segment at approximately 50 Hz and also interference 54 present at approximately 28 Hz. Similar constant amplitude 50 and 28 Hz interference, 56 and 58 in band 3, was also uniformly present in the input EOG signal. The source of the 50 Hz interference was probably mains electricity or radiation therefrom; the source of the 28 Hz interference is unknown.

The second and fourth bands in FIG. 4 demonstrate that this narrow band periodic interference at 50 and 28 Hz has been substantially removed.

Removal of this interference required first finding center frequencies and zero crossing bandwidths. FIGS. 5 and 6 illustrate the mean signal power (first bands in each figure) and its standard deviation (second bands in each figure) across a 0-64 Hz bandwidth. The first bands in both figures demonstrate visibly-present narrow band interference at center frequencies of 50 and 28 Hz. These center frequencies were automatically detected because the standard deviation of the signal power, illustrated in the second bands of both figures, was considerably less than threshold, which was chosen as one for this example. The second bands also show that in this example a less restrictive threshold for automatically recognizing narrow band periodic interference would have also been satisfactory. Zero crossing bandwidths of 3 Hz for the 50 Hz interference and 2 Hz for the 28 Hz interference were determined from the signal Fourier transforms (not illustrated).

The output signals were then constructed by doing a phase corrected inverse Fourier transform using input from which the interfering signals had been removed. Bands 2 and 4 of FIG. 4 illustrates the spectrograms of output signals. FIG. 7 illustrates the EEG and EOG signals in the time domain, where bands one and three are the unfiltered input signals and bands two and four are the filtered output signals. The output signals are clearly much improved and are sufficient without more processing for scoring sleep stages. In contrast, the input would have been difficult to score.

Next, QRS artifacts were limited or removed according to the process illustrated in FIG. 2B. FIG. 8 illustrates QRS "leakage" into the scalp recording of the EEG. Band one of this figure is the input signal after narrow band periodic interference filtering. Band two is the output of the Pan-Tompkins QRS detection algorithm applied to the input EEG signals. This algorithm generates spikes at QRS occurrences according to the steps of bandpass filtering, differentiating and integrating. Pan-Tompkins integrator output in band two and in other figures is labeled "I(t)". Band three is a coincident single channel ECG, and band four is the result of applying Pan-Tompkins to this signal. FIG. 9 illustrates similar results derived from the EOG input signal.

It is clear by comparing the Pan-Tompkins output from the EEG and EOG signals, bands one and two in FIGS. 8 and 9, with the Pan-Tompkins output from a coincident ECG, bands three and four in FIGS. 8 and 9, that there exists significant ECG leakage into these signals. Because of the synchronization of the EEG and EOG with the ECG, there can be no doubt that ECG leakage is actually present, and that this interference is not merely pulsation from a scalp vessel. Further, pulse output frequencies from the Pan-Tompkins processing can be calculated to check whether detected pulses are within a reasonable heart rate range. Here, during illustrated segment, these frequencies had a mean heart rate of 77.3 Hz with a minimum/maximum of 69.7 Hz and 87.6 Hz. These frequencies are reasonable for true QRS leakage. These figures also illustrate that a coincident ECG is not required for the present invention, as the occurrence of QRS pulses can often be detected directly in EEG and EOG signals.

Next, FIG. 10 (having an expanded temporal scale) illustrates wavelet decomposition and thresholding. Band one illustrates the Pan-Tompkins integrator output, I(t). Band two through five then illustrate the four wavelet sub-bands, each sub-band representing half the frequency of the previous sub-band. The threshold, $T_B$, is then determined from, for example, the data in FIG. 10 according to the described methods, which first locate coefficients in the vicinity of recognized QRS occurrence times and coefficients not in these vicinities. For example, temporal region 62 is in the vicinity of the third QRS occurrence indicated by Pan-Tompkins integrator output (using an expanded temporal scale). If can be appreciated that wavelet coefficients at least in sub-bands 1, 2 and 3 tend to have higher amplitude in this region as compared to outside this region and other regions in the vicinities of other QRS waves.

Thresholds can readily be determined for each sub-band that separate the larger coefficient in region 62 from the smaller coefficients outside this and similar regions. For example, threshold band 64 identifies these larger coefficients in sub-band 1, and threshold band similarly identifies larger coefficients in sub-band 3. Even tighter thresholds may be advantageous in this example. A similar threshold sub-band can be determined for sub-band 3. The QRS artifacts are less easily separated in sub-band 4. Coefficients in sub-band 4 accordingly may not be thresholded, or alternatively a generous threshold may be used.

Next, the wavelet coefficients are thresholded using the chosen thresholding function and the determined thresholds. In the example, the thresholding function of FIG. 2D was used to zero coefficients exceeding the thresholds. FIGS. 10 and 11 illustrate the results of limiting or removing QRS artifacts in the EEG signal and in the EOG signal, respectively. The first bands in both figures illustrate these signals before limiting QRS leakage artifacts. QRS leakage artifacts are quite evident in these signals as numerous, largely periodic sharp signal spikes. The second bands illustrate that after QRS removal, the interfering signal spikes are considerably limited or completely eliminated.

Finally, by comparing the original input signals in bands one and two of FIG. 7 with the final output signals in bands two of FIGS. 11 and 12, it can be appreciated how the methods of this invention lead to EEG and/or EOG signals of considerably improved quality and usefulness. Major types of interference and artifact have been removed while the EEG and EOG signals of interest have substantially been preserved without smoothing or other quality loss. This example thus illustrates that the methods of this invention can process input EEG and EOG signals into output signals that are more useful for sleep scoring in sleep studies and also for analysis of EEG signals obtained for other purposes.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

In particular, this invention includes sub-combinations of the methods and systems which have been described primarily in their preferred embodiments. For example, portions of the methods of this invention may be usefully practiced alone or in combinations with other portions.

What is claimed is:

1. A method for processing a composite physiological signal having at least one physiological signal of interest and at least one unwanted spurious signal, the composite physiological signal having a first duration, the method comprising:

determining a variable spurious signal threshold, said spurious signal threshold being determined as a function of signal spectral energy;

or eliminating at least one narrow-band spurious signal in said physiological signal throughout said signal first duration that meets or exceeds said spurious signal threshold by performing a plurality of Fourier transforms, each of said Fourier transforms being performed on at least one of a plurality of overlapping temporal windows of said physiological signal, and filtering Fourier coefficients by reducing said Fourier coefficients in narrow bands of frequencies, whereby a window-to-window temporal variation of said Fourier coefficients to be filtered is distinguishably less than a window-to-window temporal variation of non-filtered Fourier coefficients;

recreating an intermediate signal throughout substantially all of said physiological signal first duration by inverse Fourier transforming said filtered Fourier coefficients;

eliminating at least one intermittently-occurring spurious signal in said intermediate signal by performing at least one wavelet analysis on said intermediate signal, said intermittently-occurring spurious signal including a plurality of intermittently-occurring wavelet coefficients, and filtering said intermittently-occurring wavelet coefficients by reducing or zeroing intermittently-occurring wavelet coefficients that are distinguishably greater than the remaining intermittently-occurring wavelet coefficients in said intermittently-occurring spurious signal; and recreating a second physiological signal in filtered form by performing a plurality or inverse wavelet analyses on said filtered intermittently-occurring wavelet coefficients.

2. The method of claim 1 wherein Fourier coefficients are found to have a temporal variation substantially less than the temporal variation of said physiological signal if the standard deviation of said coefficients is less than a threshold.

3. The method of claim 2 wherein said threshold depends on a standard deviation of said Fourier coefficients of interest.

4. The method of claim 1 wherein said filtering Fourier coefficients further comprises determining the zero-crossing bandwidth of Fourier coefficients; and limiting the amplitudes of Fourier coefficients within said zero-crossing bandwidth.

5. The method of claim 1 wherein said filtering wavelet coefficients further comprises applying a threshold function to said wavelet coefficients.

6. The method of claims 5 wherein said threshold function sets to zero wavelet coefficients having amplitudes exceeding a threshold value.

7. The method of claim 1 further comprising performing at least one inverse Fourier transform of said filtered Fourier coefficients;

performing at least one inverse wavelet transform of said filtered wavelet coefficients; and.

outputting the signal resulting from said inverse Fourier transform and said inverse wavelet transform.

8. The method of claim 1, wherein a total temporal duration of all occurrences of said intermittently-occurring spurious signals is less than or equal to approximately one-fifth of said total temporal duration of a signal window being processed.

9. The method of claim 1 wherein said intermittently-occurring spurious signals comprise at least one occurrence of a QRS wave.

10. The method of claim 9 wherein said filtering wavelet coefficients further comprises applying a threshold function to said wavelet coefficients; and wherein said threshold value is between a first expected amplitude of wavelet coefficients not in a vicinity of any QRS wave occurrence and a second expected amplitude of distinguishable wave coefficients in the vicinity of at least one QRS wave occurrence.

11. The method of claim 10 wherein vicinities of QRS wave occurrences are determined by a QRS detection method applied to a physiological signal.

12. The method of claim 10 wherein said first and/or second expected amplitudes are determined in dependence on the means and standard deviations of wavelet coefficients.

13. The method of claim 1 wherein said physiological signals comprise one or more of electroencephalographic (EEG) signals, and/or electrooculographic (EOG) signals, and/or electromyographic (EMG) signals.

14. The method of claim 1 wherein said windows are chosen to overlap so that all portions of a physiological signal are within one or more of said windows.

15. The method of claim 1, wherein at least said Fourier coefficients are filtered by being set to zero.

16. The method of claim 1, wherein first Fourier coefficients in a narrow frequency band present in all windows have window-to-window variations that are distinguishably less than the window-to-window variations of second Fourier coefficients if the standard deviation of said first Fourier coefficients is less than a first threshold.

17. The method of claim 1 wherein a wavelet coefficient is reduced or zeroed only when approximately coincident with a QRS complex in a concurrent ECG signal.

18. A method for processing a physiological signal of interest having a certain duration and comprising unwanted spurious signals, the method comprising:

applying to said physiological signal one or more filters for producing a plurality of transform coefficients that are responsive to signal components present in sub-domains of a time/frequency domain plane having a plurality of different shapes, said filters comprising one or more windowed Fourier transformations responsive to signal components in sub-domains having a shape with a relative temporal duration substantially greater than a relative frequency bandwidth, and also comprising one or more wavelet transformations responsive to signal components in sub-domains having a limited relative temporal duration, and performing a first filtering operation that reduces or eliminates spurious signals by reducing or zeroing first Fourier transform coefficients in one or more narrow bands with a substantially constant frequency that have temporal variations distinguishably less than the temporal variations of second Fourier transform coefficients, and a second filtering operation that reduces or eliminates spurious signals by reducing or zeroing third wavelet transform coefficients with a limited relative temporal duration and with amplitudes that are distinguishably greater than the amplitudes of fourth wavelet transform coefficients; and performing a plurality of inverse transformations to recreate a signal of interest in filtered form.

19. The method claim 18 wherein applying a filter further comprises determining whether signal components present in a time/frequency sub-domain arise from spurious signals, and limiting said signal components that arise from spurious signals.

20. The method of claim 19 wherein limiting said signal components further comprises setting an amplitude of said signal components to zero.

21. The method of claim 19 wherein limiting said signal components further comprises applying a threshold function to said signal components.

22. The method of claim 19 wherein a signal component present in a time/frequency sub-domain is determined to arise from spurious signals if said signal component has a temporal variation in said sub-domain that is substantially less than the temporal variation of said physiological signal of interest.

23. The method of claim 19 wherein a signal component present in a time/frequency sub-domain is determined to arise from spurious signals if said signal component has characteristics that are statistically distinguishable from said physiological signal of interest.

24. The method of claim 18 wherein applying a filter for filtering signal components present in a time/frequency sub-domain having a shape with a relative temporal duration substantially greater than a relative frequency bandwidth further comprises performing a windowed Fourier transform.

25. The method of claim 18 wherein applying said filters further comprises applying said filters in a temporal sequence.

26. The method of claim 18 wherein said physiological signals comprise one or more of electroencephalographic (EEG) signals, and/or electrooculographic (EOG) signals, and/or electromyographic (EMG) signals, and/or electrocardiographic (ECG) signals.

27. A computer system for processing a physiological signal of interest also comprising unwanted spurious signals, the system comprising a non-transitory computer readable medium comprising encoded instructions for causing a processor to perform the steps of claim 1.

28. A computer system for processing a physiological signal of interest said physiological signal including unwanted spurious signals, said system comprising a processor and non-transitory computer readable memory having encoded instructions for causing said processor to perform the steps of claim 18.

* * * * *